(12) United States Patent
Ouchi

(10) Patent No.: US 6,572,563 B2
(45) Date of Patent: Jun. 3, 2003

(54) ENDOSCOPIC TISSUE COLLECTING INSTRUMENT

(75) Inventor: Teruo Ouchi, Saitama (JP)

(73) Assignee: Pentax Corporation, Tokyo (JP)

(*) Notice: Subject to any disclaimer, the term of this patent is extended or adjusted under 35 U.S.C. 154(b) by 0 days.

(21) Appl. No.: 09/739,117

(22) Filed: Dec. 19, 2000

(65) Prior Publication Data

US 2001/0005778 A1 Jun. 28, 2001

(30) Foreign Application Priority Data

Dec. 22, 1999 (JP) .......................... 11-363609
Jan. 18, 2000 (JP) ......................... 2000-008439

(51) Int. Cl.⁷ ............................................. A61B 10/00
(52) U.S. Cl. .................................. 600/564; 606/167
(58) Field of Search ................................ 600/564, 566, 600/567, 568, 565; 606/167, 104, 106, 171; 604/272

(56) References Cited

U.S. PATENT DOCUMENTS

| | | | | |
|---|---|---|---|---|
| 3,477,423 A | * | 11/1969 | Griffith | 128/2 |
| 4,543,966 A | * | 10/1985 | Islam et al. | 128/754 |
| 4,702,261 A | * | 10/1987 | Cornell et al. | 128/754 |
| 4,708,147 A | * | 11/1987 | Haaga | 128/753 |
| 5,197,484 A | * | 3/1993 | Kornberg et al. | 128/754 |
| 5,487,392 A | | 1/1996 | Haaga | 128/753 |
| 5,601,533 A | | 2/1997 | Hancke et al. | 604/164 |
| 5,649,547 A | * | 7/1997 | Ritchart et al. | 128/754 |
| 5,718,237 A | | 2/1998 | Haaga | 128/751 |
| 5,741,287 A | * | 4/1998 | Alden et al. | 606/170 |
| 5,989,196 A | * | 11/1999 | Chu et al. | 600/567 |

FOREIGN PATENT DOCUMENTS

JP 10216134 8/1998

* cited by examiner

*Primary Examiner*—Charles G. Freay
*Assistant Examiner*—Han L. Liu
(74) *Attorney, Agent, or Firm*—Greenblum & Bernstein, P.L.C.

(57) ABSTRACT

An endoscopic tissue collecting instrument is provided, which can collect a large tissue specimen by cutting the tissue positively with a blade of an outer sheath. The blade formed at the distal end of the outer sheath is directed oblique to the circumferential direction of the outer sheath.

14 Claims, 19 Drawing Sheets

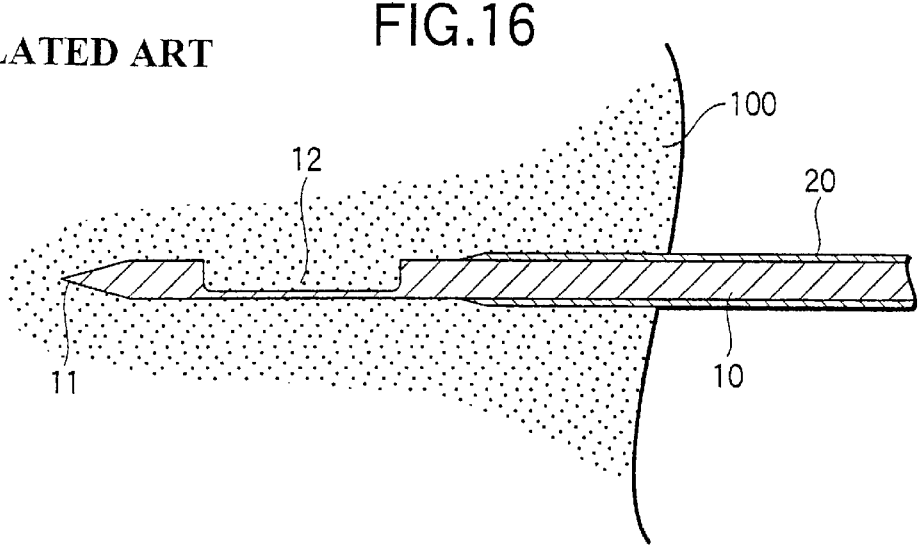
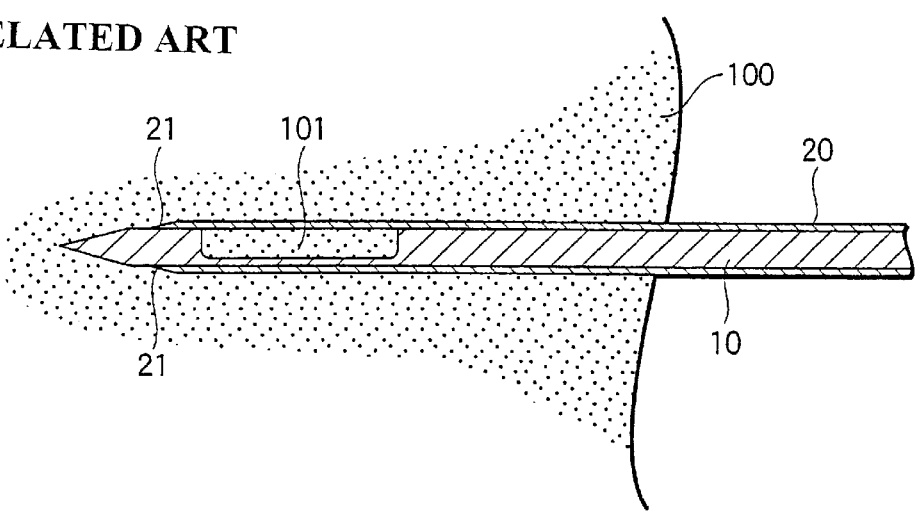
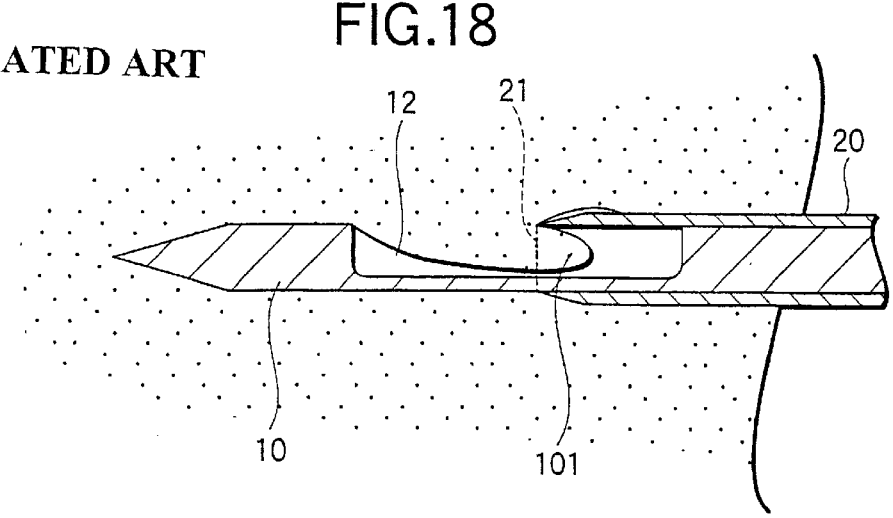

ENDOSCOPIC TISSUE COLLECTING INSTRUMENT

BACKGROUND OF THE INVENTION

The present invention relates to an endoscopic tissue collecting instrument suitable for use typically in a biopsy of the pancreas, the liver and other organ by being inserted into and removed from a treatment instrument insertion channel in an endoscope.

FIG. 15 shows the distal end portion of a Menghini needle used as an endoscopic tissue collecting instrument. The Menghini needle comprises a rod-shaped needle shaft 10 having a pointed end 11 and a tissue retaining recess 12 formed in the lateral side of an area close to the needle end 11 and into which an excised tissue specimen is retained.

A cannula or outer sheath 20 is fitted over the needle shaft 10 to be capable of moving back and forth along the longitudinal axis, and it has an annular blade 21 formed on the inner circumference of the tip for cutting off or excise the tissue retained in the recess 12.

FIGS. 16 and 17 show how a tissue specimen for biopsy is collected with the endoscopic tissue collecting instrument thus constructed as the Menghini needle. First, as shown in FIG. 16, the outer sheath 20 pierced into the tissue 100 is pulled back a little so that the desired portion of the tissue 100 is caught in the recess 12. Then, as shown in FIG. 17, the outer sheath 20 is quickly pushed forward to cut off the retained portion of the tissue 100 as a tissue specimen 101.

This endoscopic tissue collecting instrument is designed such that the blade 21 cuts off or excises the tissue 100 perpendicularly to a direction in which the outer sheath 20 is pushed forward. For this reason, in practice, when the outer sheath 20 is being pushed forward, the tissue 100 is also pushed forward as shown in FIG. 18, and it often occurs that only a small volume of the tissue specimen 101 can be collected in the recess 12.

SUMMARY OF THE INVENTION

An object, therefore, of the present invention is to provide an endoscopic tissue collecting instrument which can collect a large tissue specimen by cutting the tissue positively with a blade provided to the outer sheath.

An endoscopic tissue collecting instrument according to the present invention is designed so that a blade can apply a cutting force to a tissue obliquely.

For example, a blade is formed at the distal end of an outer sheath to be oblique to the circumferential direction of the outer sheath. Because of this design, if the outer sheath is pushed forward to cut off a tissue, the blade slides obliquely relative to the tissue as it advances. Accordingly, the tissue can be severed without being pushed forward by the outer sheath and instead it is cut positively enough to permit the collection of a large volume of tissue specimen.

For example, a blade formed at the distal end of the outer sheath rotates about the longitudinal axis while moving along it over the tissue retaining recess. As a result, the tissue of interest is not pushed forward but can be cut easily and positively to collect a large volume of tissue specimen.

Preferably, an endoscopic tissue collecting instrument includes a needle shaft having a needle tip pointed forward, and a tissue retaining recess recessed laterally in an area close to the needle tip, and an outer sheath fitted over the needle shaft so as to be movable back and forth in a longitudinal axis direction relative to the needle shaft. The outer sheath has a blade at its distal end for cutting off a tissue retained in the tissue retaining recess. The blade formed at the distal end of the outer sheath is oriented obliquely relative to a circumferential direction of the outer sheath.

A radially inner edge of the distal end of the outer sheath may be saw-toothed to define the blade, or the distal end of the outer sheath may be obliquely cut to define the blade.

Preferably, an endoscopic tissue collecting instrument includes a needle shaft having a needle tip pointed forward, and a tissue retaining recess recessed laterally in an area close to the needle tip, and an outer sheath fitted over the needle shaft so as to be movable back and forth in a longitudinal axis direction relative to the needle shaft. The outer sheath having a blade at its distal end for cutting off a tissue retained in the tissue retaining recess. When the blade is moved across the tissue retaining recess, the outer sheath is rotated about the longitudinal axis direction while being moved in the longitudinal axis direction.

The outer sheath may be movably passed through a support tube to be fixed to an entrance of a treatment instrument insertion channel of an endoscope, and a tab projecting from a basal end portion of the outer sheath may be in engagement with a spiral groove formed in the support tube.

In this case, a slider knob may be provided for manipulation to move the tab in the longitudinal axis direction, or a rotating knob may be provided for manipulation to rotate the tab about the longitudinal axis direction.

An aspiration channel may be provided to extend through the needle shaft, and communicate with a rear of the tissue retaining recess.

The present disclosure relates to the subject matter contained in Japanese patent application Nos. Hei. 11-363609 (filed on Dec. 22, 1999), and 2000-8439 (filed on Jan. 18, 2000), which are expressly incorporated herein by reference in their entireties.

BRIEF DESCRIPTION OF THE DRAWINGS

FIG. 16 is a longitudinal section showing the distal end portion of the related endoscopic tissue collecting instrument as it is in the first phase of use;

FIG. 17 is a longitudinal section showing the distal end portion of the related endoscopic tissue collecting instrument as it is in the second phase of use;

FIG. 18 is a longitudinal section showing the distal end portion of the related endoscopic tissue collecting instrument as it is in the third phase of use;

DESCRIPTION OF THE PREFERRED EMBODIMENT

Preferred embodiments of the present invention are described below with reference to accompanying drawings.

Figure 1:
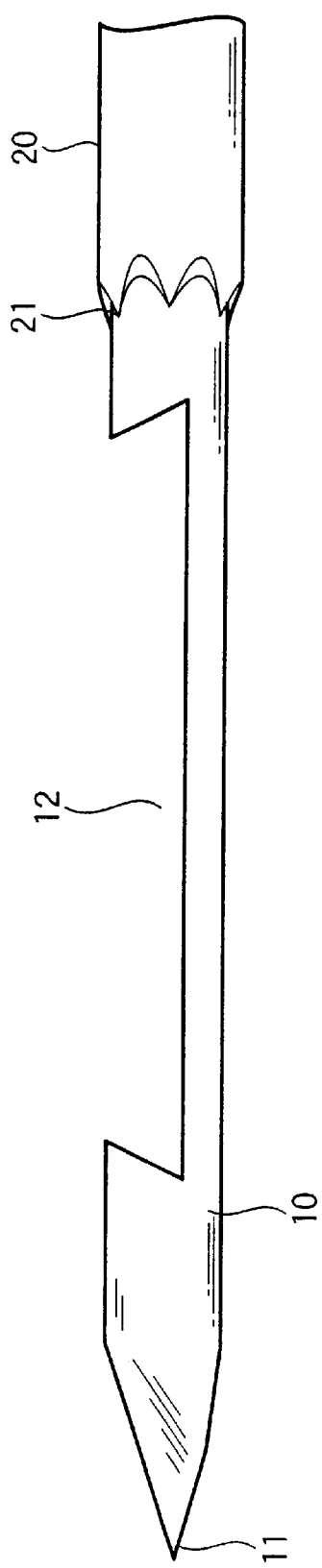
FIG. 1 is a side view showing the distal end portion of an endoscopic tissue collecting instrument according to a first embodiment of the invention.
Figure 2:
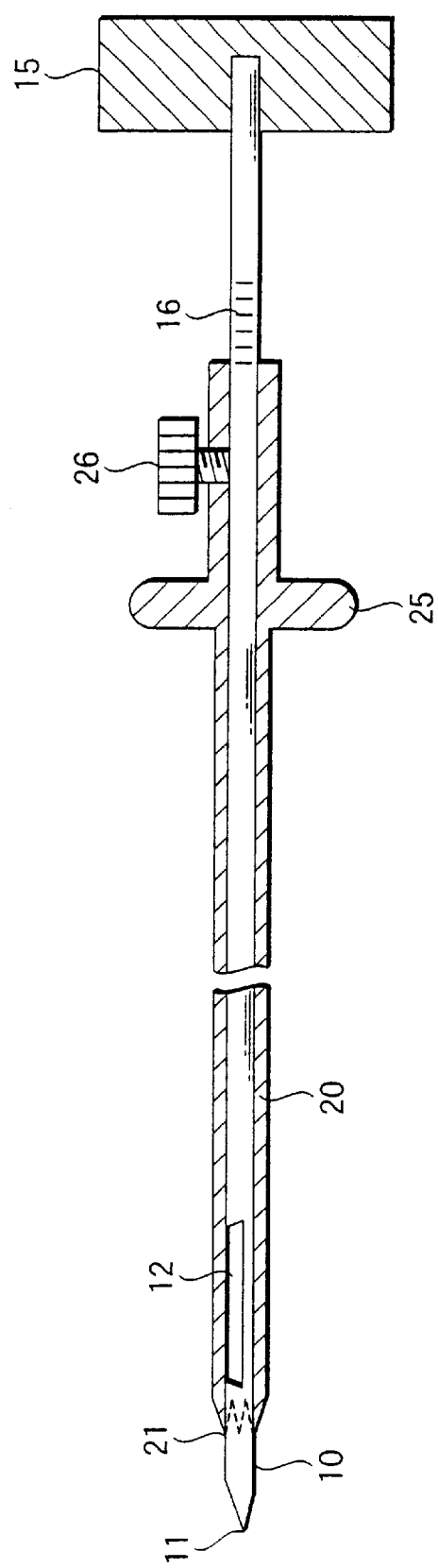
FIG. 2 is a longitudinal section showing the general layout of the endoscopic tissue collecting instrument with a tissue retaining recess being closed.
Figure 3:
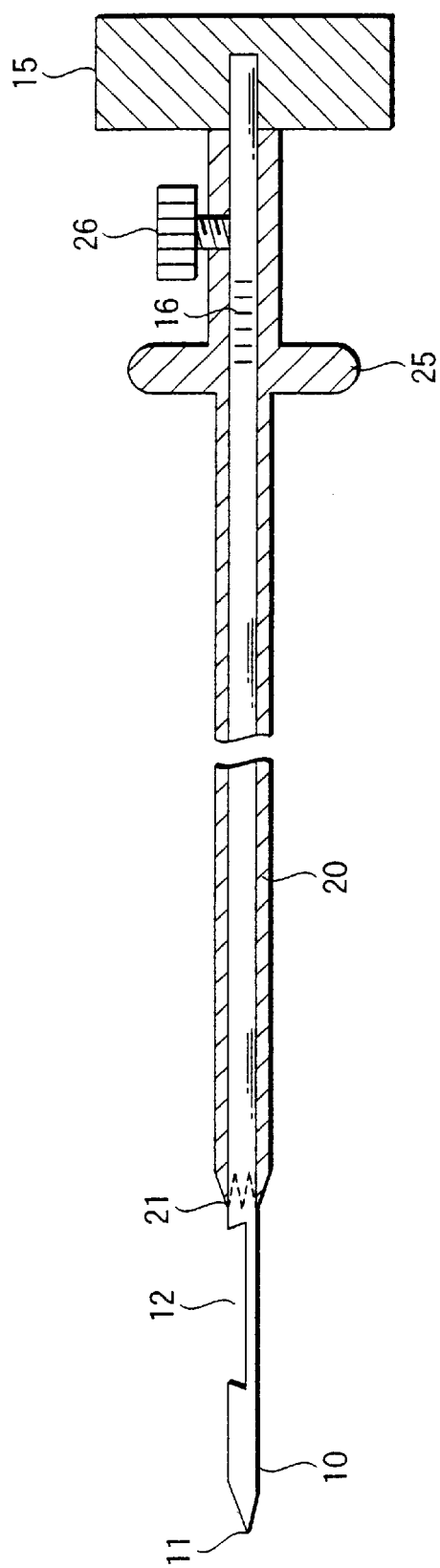
FIG. 3 is a longitudinal section showing the general layout of the endoscopic tissue collecting instrument with the tissue retaining recess being open.

FIG. 1 shows the distal end portion of an endoscopic tissue collecting instrument according to a first embodiment of the invention. FIGS. 2 and 3 show the general layout of the endoscopic tissue collecting instrument, with a cannula or outer sheath 20 being pushed to the predetermined foremost position (see FIG. 2) or pulled toward the operator (see FIG. 3).

A needle shaft 10 has a tip 11 at the distal end such that it is pointed forward. A recess 12 for retaining a collected tissue is formed in the lateral side of the needle shaft 10 in an area immediately behind the needle tip 11.

The outer sheath 20 in tubular form is fitted over the substantially entire length of the needle shaft 10 so that the outer sheath 20 is capable of moving back and forth along the longitudinal axis relative to the needle shaft 10. The needle shaft 10 and the outer sheath 20 are both formed of relatively rigid but flexible plastics. If desired, the outer sheath 20 may be formed of a thin-walled stainless steel pipe or the like.

Figure 4:
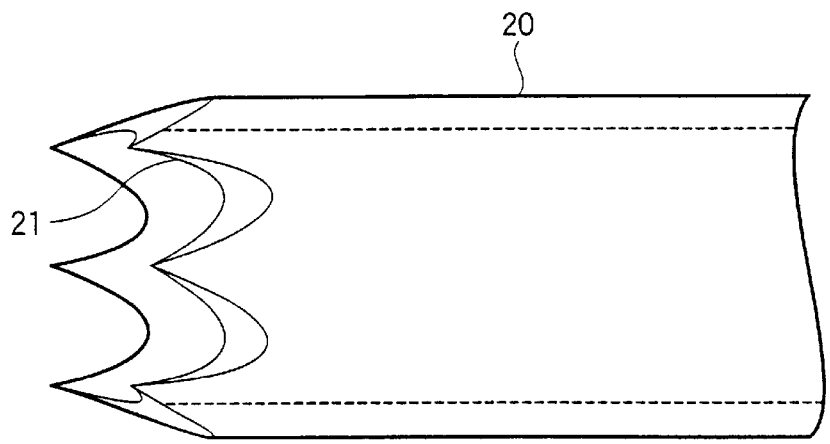
FIG. 4 is a perspective view showing the distal end portion of an outer sheath of the endoscopic tissue collecting instrument.

The distal end portion of the outer sheath 20 (which is also shown enlarged in FIG. 4) is tapered entirely, and jaggy like a saw-toothed edge.

As a result, the inner ridge portions of the saw-toothed edge located on the inner circumference at the distal end of the outer sheath 20 constitute a blade 21. Hence, the blade 21 is oblique to the periphery of the outer sheath 20 (to the circumferential direction of the outer sheath 20 in a plane taken normal to the longitudinal axis).

The outer sheath 20 is formed slightly shorter than the needle shaft 10 (typically by about 2–10 cm) and a manual locking screw 26 is fitted in the end portion closer to the operator such that its tip contacts the outer circumference of the needle shaft 10.

If the locking screw 26 is tightened, the outer sheath 20 becomes fixed to the needle shaft 10; if it is loosened, the outer sheath 20 becomes free to move back and forth relative to the needle shaft 10. A finger retaining members 15 and 25 are respectively formed on the operator side end portion of the needle shaft 10 and the operator side end portion of the outer sheath 20. By holding these finger retaining members with fingers, the operator can easily manipulate the needle shaft 10 and the outer sheath 20 to move back and forth.

An index 16 is provided on the outer surface of an area of the needle shaft 10 that is closer to the operator; by seeing how far the index 16 is from the end face of the outer sheath 20 which is closer to him, the operator can determine where the distal end of the outer sheath 20 is located relative to the needle shaft 10.

The endoscopic tissue collecting instrument thus constructed according to the first embodiment is put to service after being inserted into the treatment instrument insertion channel of an endoscope, an ultrasonic endoscope and so forth. Note that in order to prevent the needle tip 11 from damaging the treatment instrument insertion channel while it is being inserted into or removed from the latter, the endoscopic tissue collecting instrument of the invention may first be passed through a guide tube typically made of a tetrafluoroethylene resin.

Figure 5:
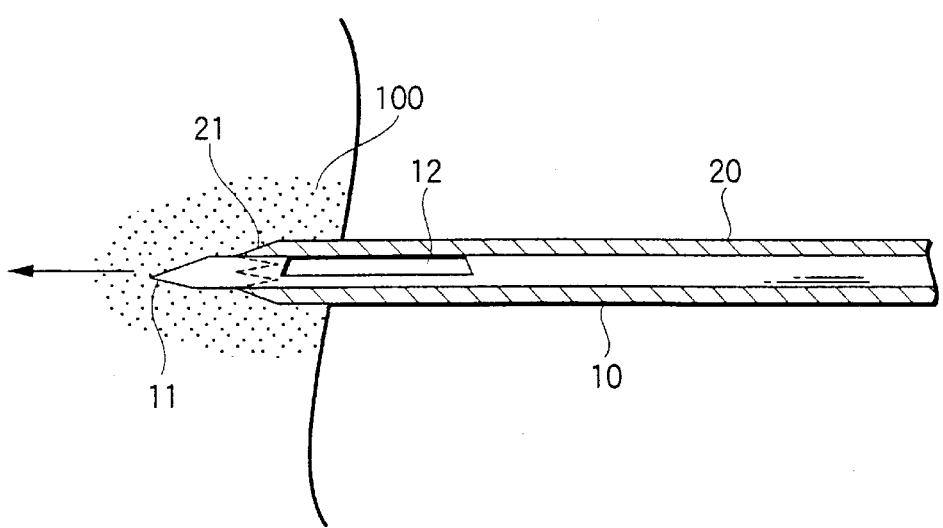
FIG. 5 is a longitudinal section showing the distal end portion of the endoscopic tissue collecting instrument as it is in the first phase of use.
Figure 6:
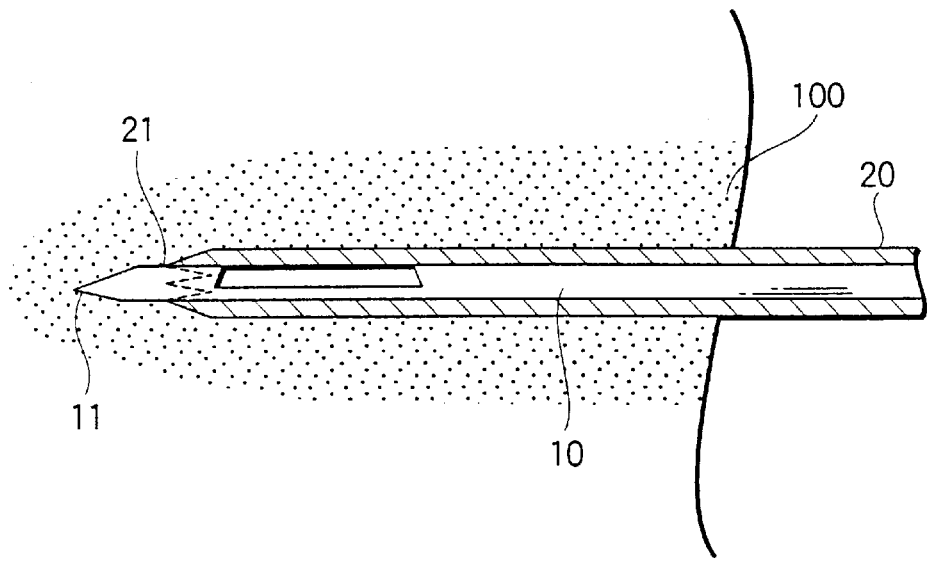
FIG. 6 is a longitudinal section showing the distal end portion of the endoscopic tissue collecting instrument as it is in the second phase of use.

FIGS. 5 to 9 show how a tissue specimen for biopsy is collected from the liver, the pancreas or other organ by means of the endoscopic tissue collecting instrument according to the first embodiment. First, as shown in FIG. 5, the distal end of the outer sheath 20 is set near the distal end of the needle shaft 10 so that the tissue retaining recess 12 is closed with the outer sheath 20, and with the locking screw 26 tightened, the needle tip 11 is pierced into the tissue 100.

Figure 7:
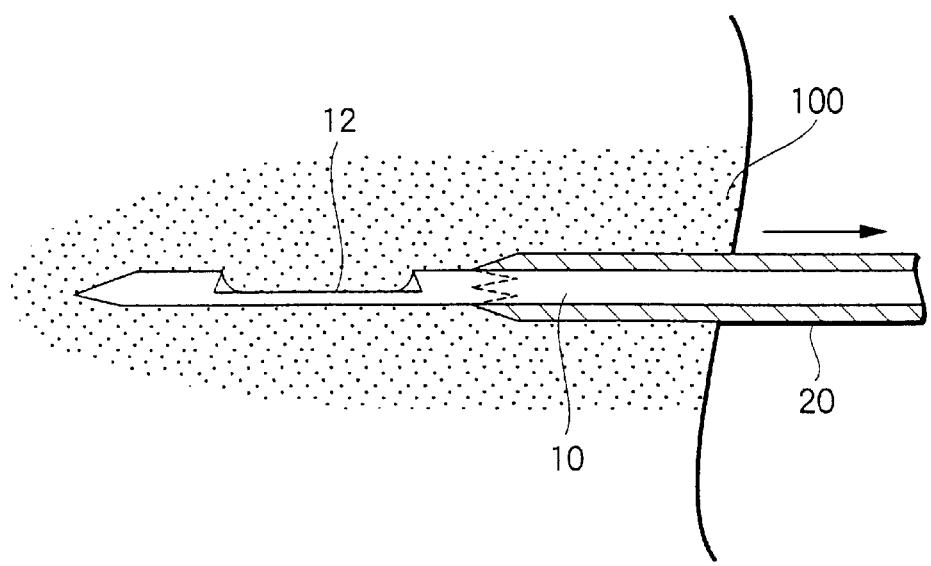
FIG. 7 is a longitudinal section showing the distal end portion of the endoscopic tissue collecting instrument as it is in the third phase of use.

When the tissue retaining recess 12 has reached a predetermined position in the tissue (see FIG. 6), the locking screw 26 is loosened and the outer sheath 20 is pulled a little toward the operator until the tissue retaining recess 12 becomes exposed as shown in FIG. 7, whereupon the tissue 100 gets into the recess 12.

Figure 8:
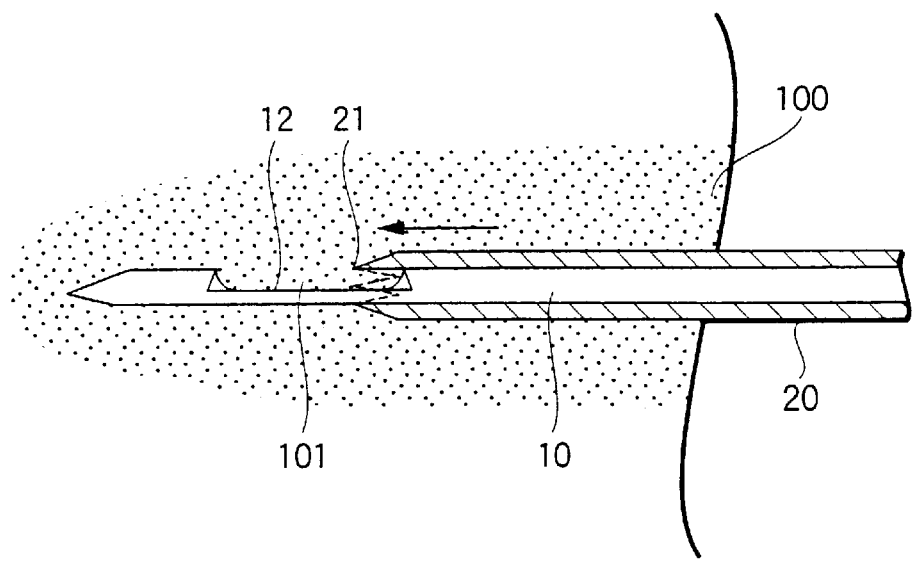
FIG. 8 is a longitudinal section showing the distal end portion of the endoscopic tissue collecting instrument as it is in the fourth phase of use.
Figure 9:
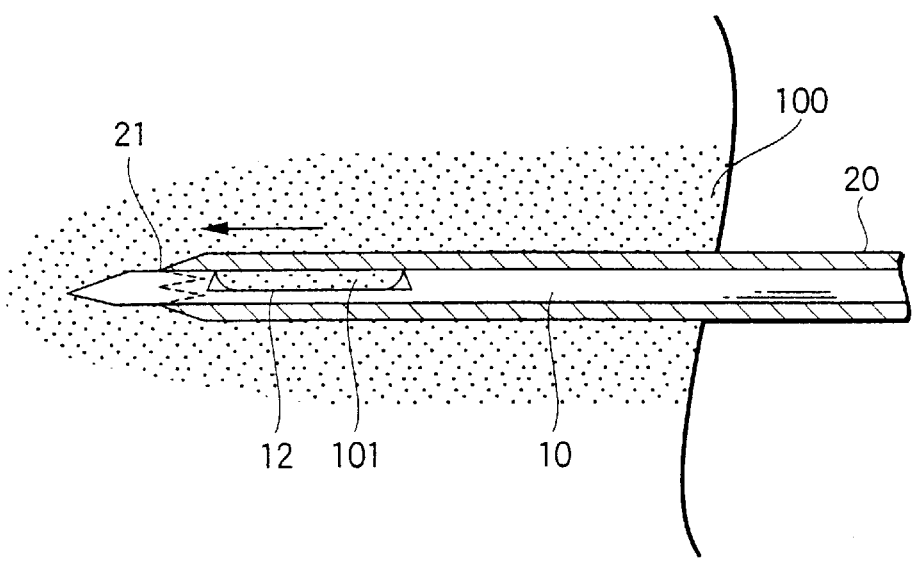
FIG. 9 is a longitudinal section showing the distal end portion of the endoscopic tissue collecting instrument as it is in the fifth phase of use.

Subsequently, the outer sheath 20 is pushed forward as shown in FIG. 8, whereupon the root of the tissue 100 which has entered the recess 12 (to become a tissue specimen 101) is severed with the blade 21 formed at the tip of the outer sheath 20.

Figure 29:
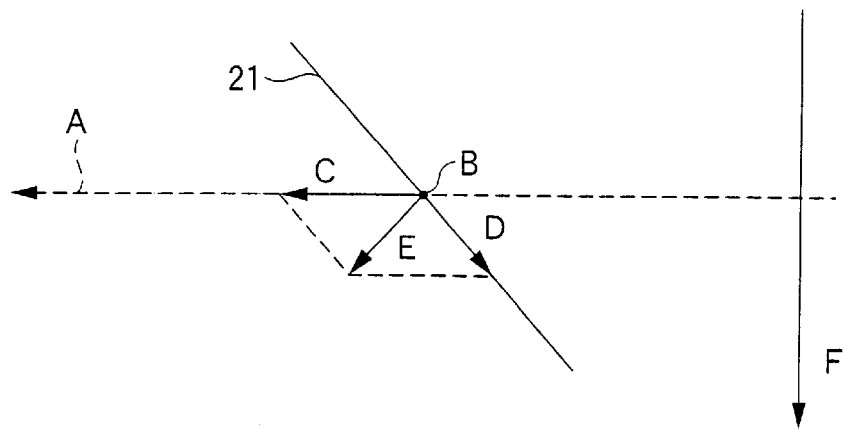
FIG. 29 is a schematic diagram showing a technical concept employed in the first embodiment.

Since the blade 21 is oriented obliquely relative to the direction in which the outer sheath 20 is pushed, the blade 21 slides obliquely relative to the tissue 100 as it moves forward and this ensures cutting of the tissue 100 without pushing the tissue 100 forward. This effect is schematically illustrated in FIG. 29. In FIG. 29, character A denotes the direction in which the outer sheath 20 is pushed, character B denotes a part of the blade 21 oriented obliquely relative to the direction in which the outer sheath 20 is pushed, and character F denotes the circumferential direction of the outer sheath 20. By pushing the outer sheath 20, i.e. the blade 21, in the direction A, the point B of the blade 21 causes a vector component C along the direction A and a vector component D along the blade 21, which are combined together as a cutting force E for positively cutting the tissue 100.

In addition, since the sharp points of the saw-toothed edge first rupture the mucosa surface, the tissue can subsequently be cut off in a smooth way.

Then, the outer sheath 20 is pushed to the farthest end so that it returns to the initial state (see FIG. 9), whereupon the tissue specimen 101 is severed from the rest of the tissue 100 with the blade 21 of the outer sheath 20 and retained within the recess 12. In this way, the tissue specimen 101 is easily collected.

Figure 10:
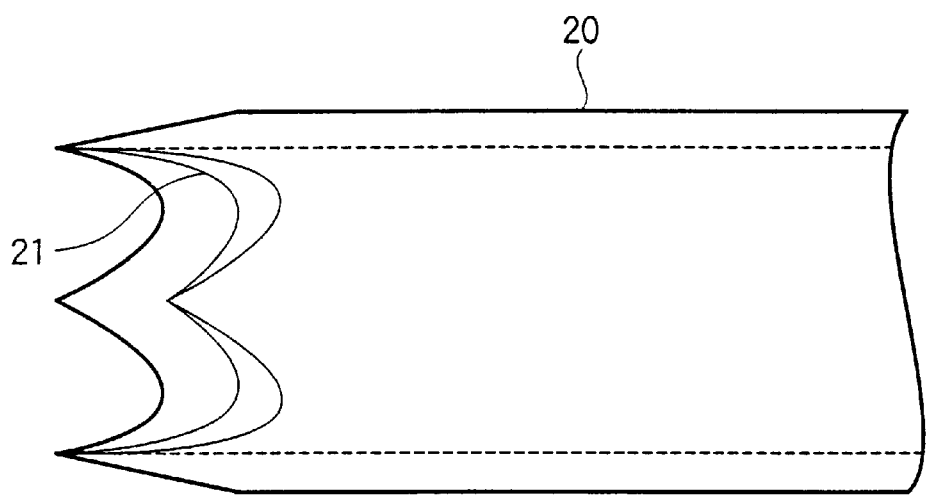
FIG. 10 is a perspective view showing the distal end portion of an outer sheath of an endoscopic tissue collecting instrument according to a second embodiment of the invention.

In the first embodiment, the blade 21 of the outer sheath 20 has six sharp points. However, the number of sharp points on the blade is variable and may be four as shown in FIG. 10 or any other number.

Figure 11:
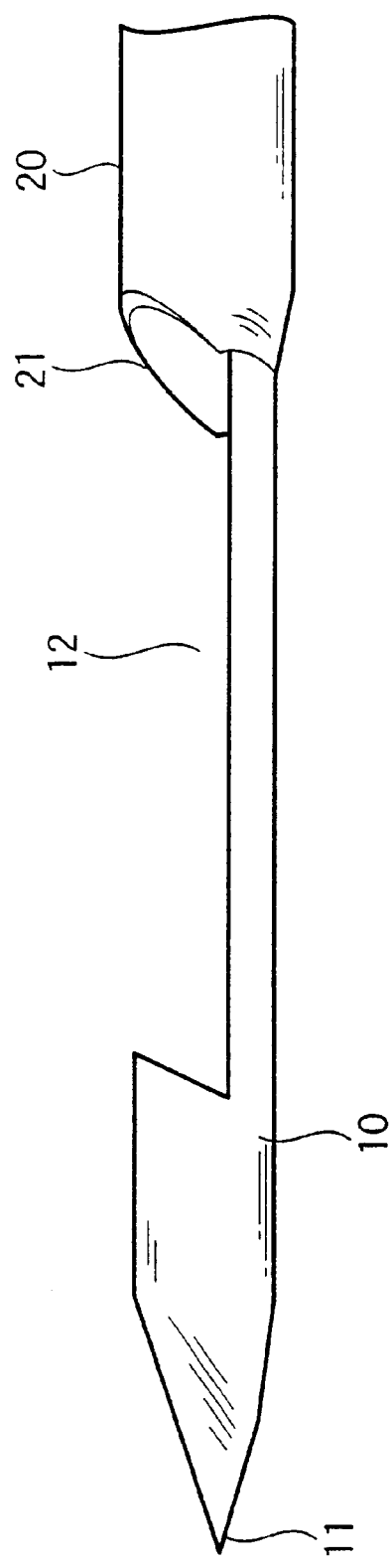
FIG. 11 is a side view showing the distal end portion of an endoscopic tissue collecting instrument according to a third embodiment of the invention.

The blade 21 of the outer sheath 20 need not be saw-toothed. For example, as shown in FIG. 11, the blade 21 may be formed such that the tip of the outer sheath 20 is cut at an oblique angle and a ridge on the inner periphery of the resultant tip of the outer sheath 20 serves as the blade 21. Even in this case, the blade 21 slides obliquely to the tissue 100 as it advances and the tissue 100 can be severed without being pushed out of the recess 12.

In the embodiment shown in FIG. 11, the blade 21 is slanted rearwardly as it is away from a bottom of the recess 12. The effect is the same if the blade 21 is slanted forwardly as it is away from the bottom of the recess 12 as shown in FIG. 12.

Figure 12:
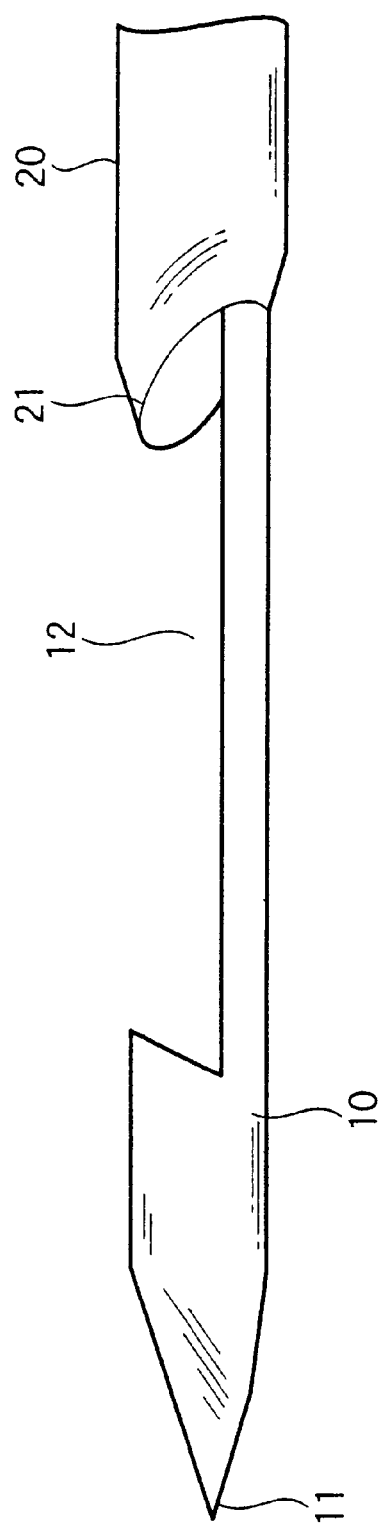
FIG. 12 is a side view showing the distal end portion of an endoscopic tissue collecting instrument according to a fourth embodiment of the invention.
Figure 13:
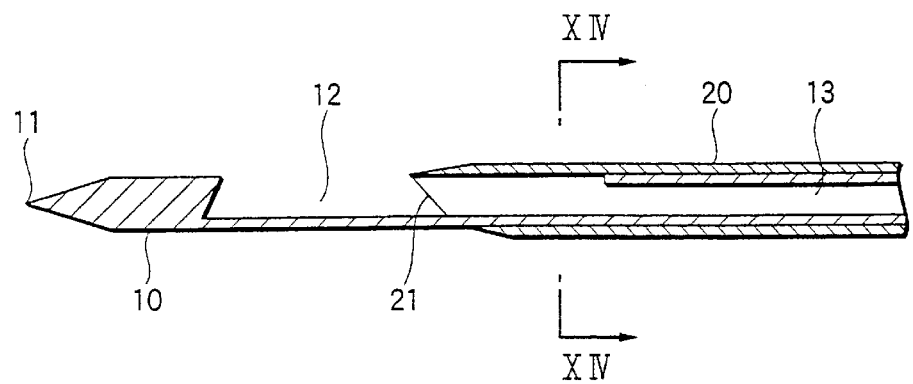
FIG. 13 is a longitudinal section showing the distal end portion of the endoscopic tissue collecting instrument according to the fourth embodiment of the invention.
Figure 14:
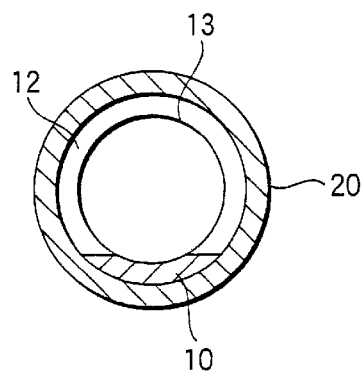
FIG. 14 is section XIV—XIV of FIG. 13.
Figure 15:
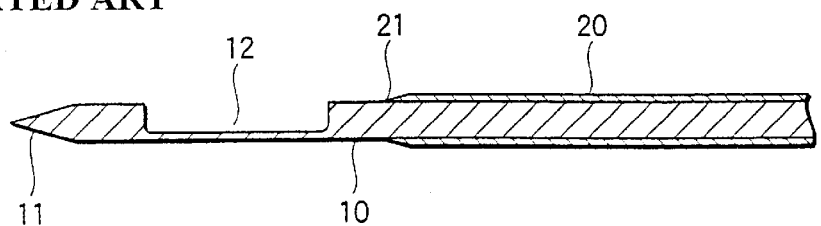
FIG. 15 is a longitudinal section showing the distal end portion of a related endoscopic tissue collecting instrument.

In addition, the embodiment shown in FIG. 12 has an aspiration channel 13 formed through the needle shaft 10 to communicate with the tissue retaining recess 12 at the distal end thereof as shown in FIG. 13. Accordingly, the tissue 100 can be sucked into the recess 12 before it is severed with the blade 21 of the outer sheath 20. FIG. 14 is section XIV—XIV of FIG. 13.

Figure 19:
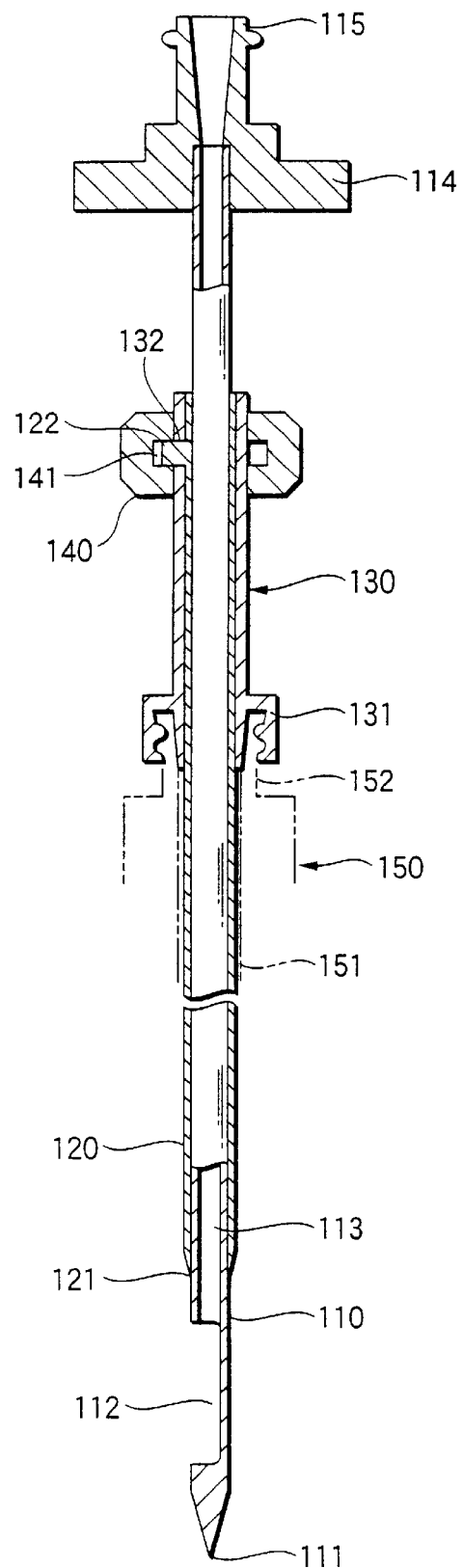
FIG. 19 is a longitudinal section of an endoscopic tissue collecting instrument according to a fifth embodiment of the invention with a tissue retaining recess being open.

FIG. 19 shows an endoscopic tissue collecting instrument according to a fifth embodiment of the invention. In FIG. 19, a cannula or outer sheath 120 is shown to have been pulled most close to the operator.

A needle shaft 110 has a solid tip 111 at the distal end such that it is pointed forward. A recess 112 for retaining a collected tissue is formed in the lateral side of the needle shaft 110 in an area immediately behind the needle tip 111.

An aspiration channel 113 that communicates with the tissue retaining recess 112 is formed through the entire length of the part of the needle shaft 110 which is rearward of the recess 112. Hence, that part of the needle shaft 110 which is rearward of the recess 112 is in pipe form. The aspiration channel 113 is not essential to the present invention and may be omitted.

A knob 114 is fitted at the basal end of the needle shaft 110. The operator holds the knob 114 between the fingers and manipulates the needle shaft 110 to move back and forth along the longitudinal axis. An aspiration socket 115 to which an aspirating device (not shown) can be connected is formed as an integral part of the knob 114 so that vacuum can be drawn through the aspiration channel 113.

The outer sheath 120 is fitted over the substantially entire length of the needle shaft 110, and the outer sheath 120 is capable of not only moving back and forth along the longitudinal axis but also rotating about it. The distal end portion of the outer sheath 120 is tapered such that an annular blade 121 is formed on the inner circumference of the outer sheath 120 at its distal end. In this embodiment, the annular blade 121 extends in the circumferential direction of the outer sheath 112 in a plane normal to the longitudinal axis.

The area of the outer sheath 120 which is near its basal end is loosely passed through a support tube 130. A mounting socket 131 is formed as an integral part of the support tube 130 in the distal end portion. The socket 131 is typically in the form of a Luer-Lok female socket and can be fixed to or disengaged from an entrance socket 152 of a treatment instrument insertion channel 151 of an endoscope. Indicated by 150 is the manipulating section of an endoscope.

Figure 20:
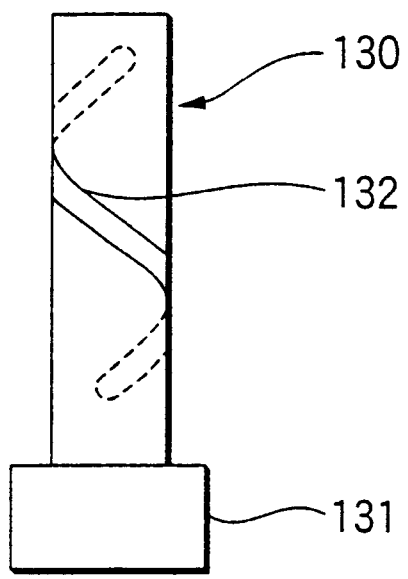
FIG. 20 is a side view of the support tube in the endoscopic tissue collecting instrument according to the fifth embodiment.

The support tube 130 is generally cylindrical, and a spiral groove 132 is formed in the surface of its side wall as shown in FIG. 20. The pitch and length of the spiral groove 132 are variable, and appropriate values may be selected.

Turning back to FIG. 19, a tab 122 projecting laterally from the basal end of the outer sheath 120 is in engagement with the spiral groove 132. Hence, with the support tube 130 being fixed to the entrance socket 152 of the treatment instrument insertion channel 151, the outer sheath 120 moves back and forth along the longitudinal axis while rotating about it. The inner positioned needle shaft 110 is independently manipulated by means of the knob 114.

The support tube 130 is fitted with a slider knob 140 on its circumference that is capable of rotation about the longitudinal axis. A circumferential groove 141 that engages the head of the tab 122 passing through the spiral groove 132 is formed in the inner surface of the slider knob 140. If the operator holds the slider knob 140 between the fingers and manipulates it to move along the longitudinal axis, the outer sheath 120 moves back and forth along the longitudinal axis while rotating about it.

FIG. 19 shows the slider knob 140 in its most retracted state, in which the annular blade 121 at the tip of the outer sheath 120 is rearward of the tissue retaining recess 112.

Figure 21:
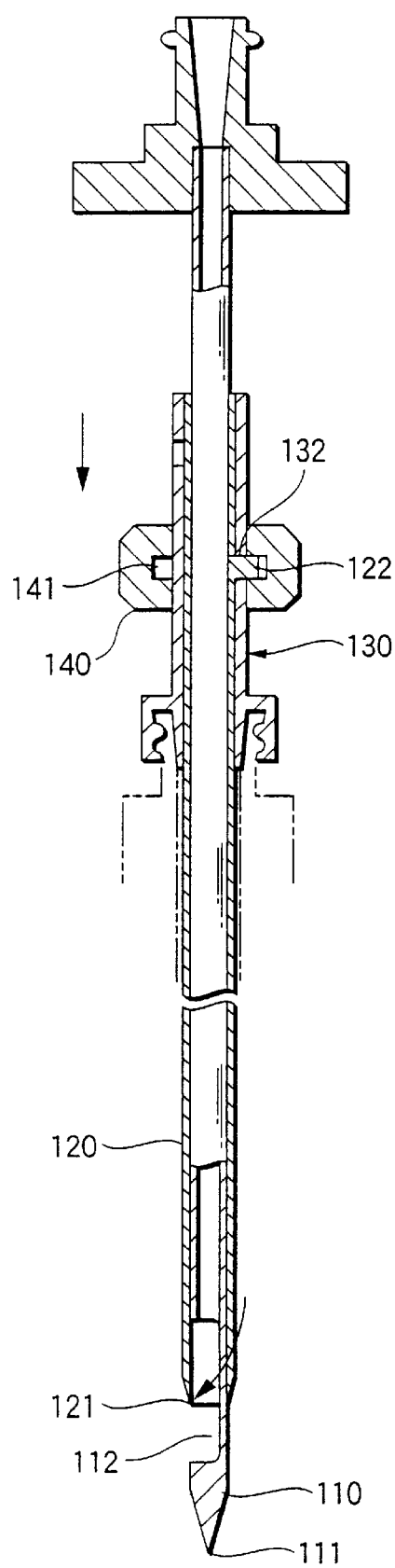
FIG. 21 is a longitudinal section of the endoscopic tissue collecting instrument with the tissue retaining recess being half closed according to the fifth embodiment.
Figure 22:
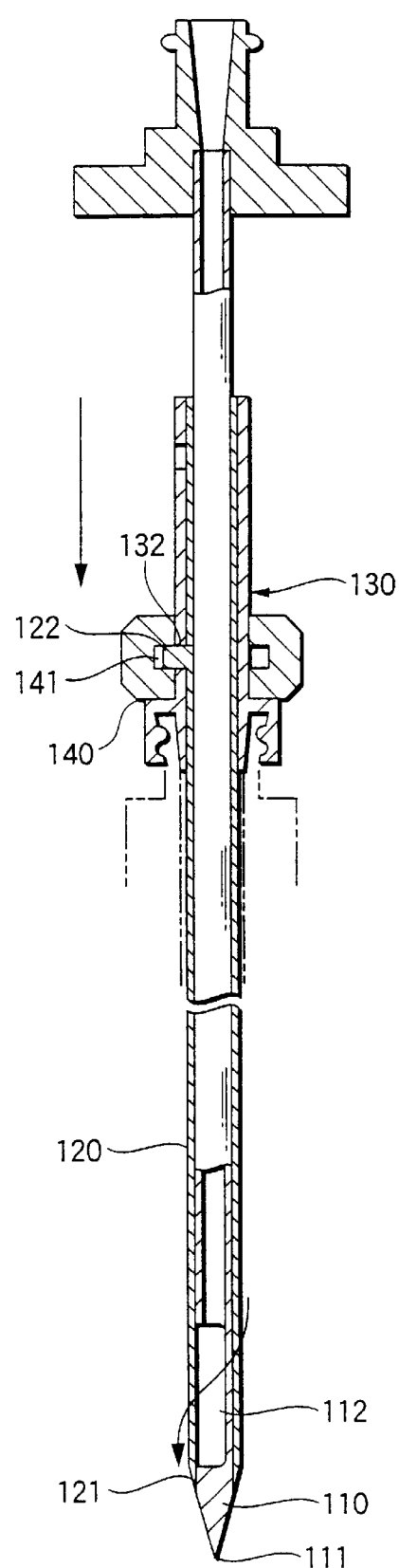
FIG. 22 is a longitudinal section of the endoscopic tissue collecting instrument with the tissue retaining recess being completely closed according to the fifth embodiment.

If the slider knob 140 is slid away from the operator, the annular blade 121 of the outer sheath 120 rotates about the longitudinal axis as it moves forward over the surface of the tissue retaining recess 112 as shown in FIG. 21. If the slider knob 140 has reached the most advanced position, the annular blade 121 moves to a position ahead of the tissue retaining recess 112.

The endoscopic tissue collecting instrument thus constructed according to the fifth embodiment is put to service after being inserted into the treatment instrument insertion channel 151 of an endoscope, an ultrasonic endoscope and so forth. Note that in order to prevent the needle tip 111 from damaging the treatment instrument insertion channel 151 while it is being inserted into or removed from the latter, the endoscopic tissue collecting instrument of the invention may first be passed through a guide tube typically made of a tetrafluoroethylene resin.

Figure 23:
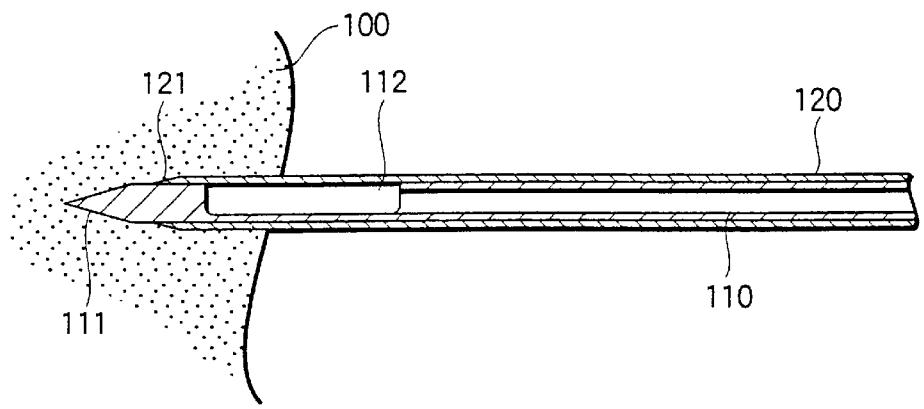
FIG. 23 is a longitudinal section showing the distal end portion of the endoscopic tissue collecting instrument according to the fifth embodiment as it is in the first phase of use.
Figure 24:
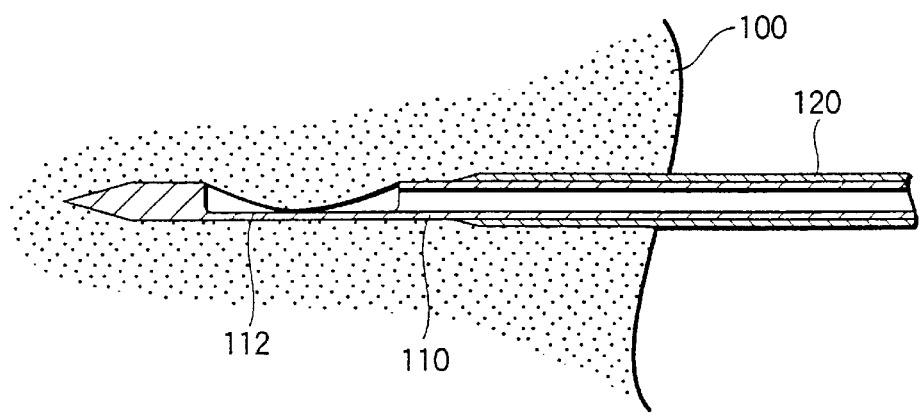
FIG. 24 is a longitudinal section showing the distal end portion of the endoscopic tissue collecting instrument according to the fifth embodiment as it is in the second phase of use.

FIGS. 23 to 27 show how a tissue specimen for biopsy is collected from the liver, the pancreas or other organ by means of the endoscopic tissue collecting instrument according to the fifth embodiment. First, as shown in FIG. 23, the distal end of the outer sheath 120 is set near the distal end of the needle shaft 110 so that the tissue retaining recess 112 is closed with the outer sheath 120, and with the locking screw 126 tightened, the needle tip 111 is pierced into the tissue 100.

When the tissue retaining recess 112 has reached a predetermined position in the tissue (see FIG. 24), the outer sheath 120 is pulled toward the operator until the tissue retaining recess 112 becomes exposed, whereupon the tissue 100 gets into the recess 112.

Figure 25:
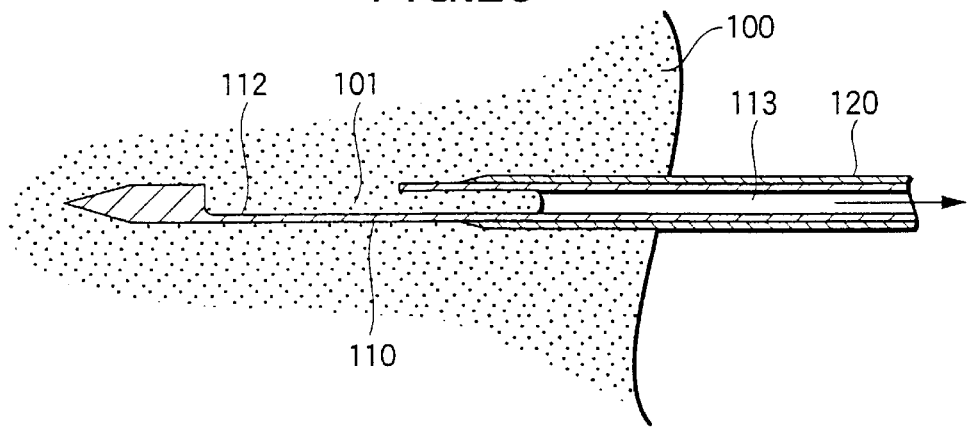
FIG. 25 is a longitudinal section showing the distal end portion of the endoscopic tissue collecting instrument according to the fifth embodiment as it is in the third phase of use.

Then, an aspirating device (not shown) is activated and vacuum is drawn from the tissue retaining recess 112 via the aspiration channel 113. As shown in FIG. 25, the tissue 100 from which a tissue specimen 101 is to be severed is sucked into every part of the tissue retaining recess 112 and further inward to reach the area near the entrance of the aspiration channel 113.

Figure 26:
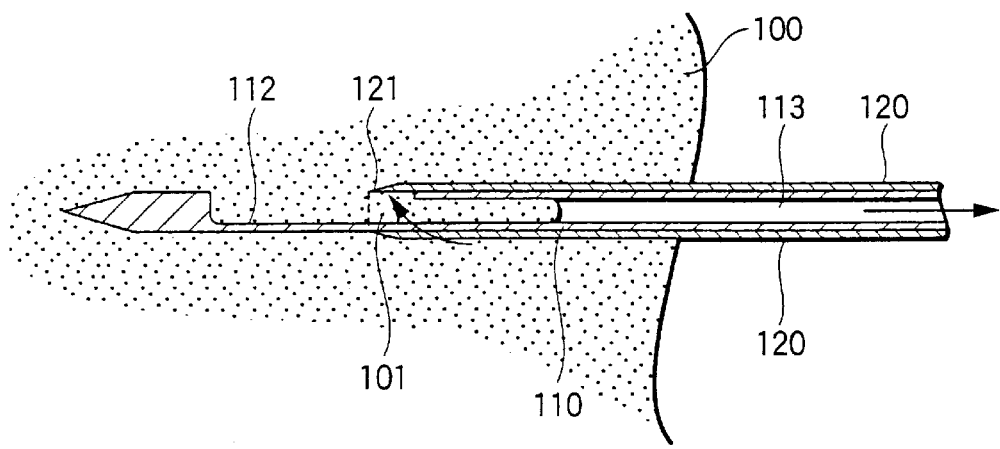
FIG. 26 is a longitudinal section showing the distal end portion of the endoscopic tissue collecting instrument according to the fifth embodiment as it is in the fourth phase of use.
Figure 27:
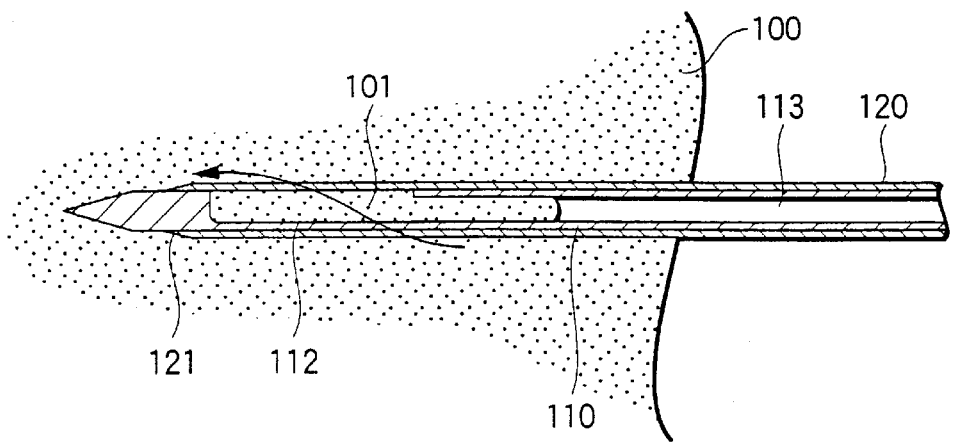
FIG. 27 is a longitudinal section showing the distal end portion of the endoscopic tissue collecting instrument according to the fifth embodiment as it is in the fifth phase of use.

Subsequently, the slider knob 140 is pushed forward, whereupon the annular blade 121 of the outer sheath 120 rotates about the longitudinal axis as it is cutting the tissue specimen 101 from the rest of the tissue 100 (see FIGS. 26 and 27). This cutting action is obtained not only by the pushing of the blade 121 along the longitudinal axis but also by the sliding of the blade 21 in the circumferential direction, and consequently the tissue 100 can be cut off easily.

Figure 30:
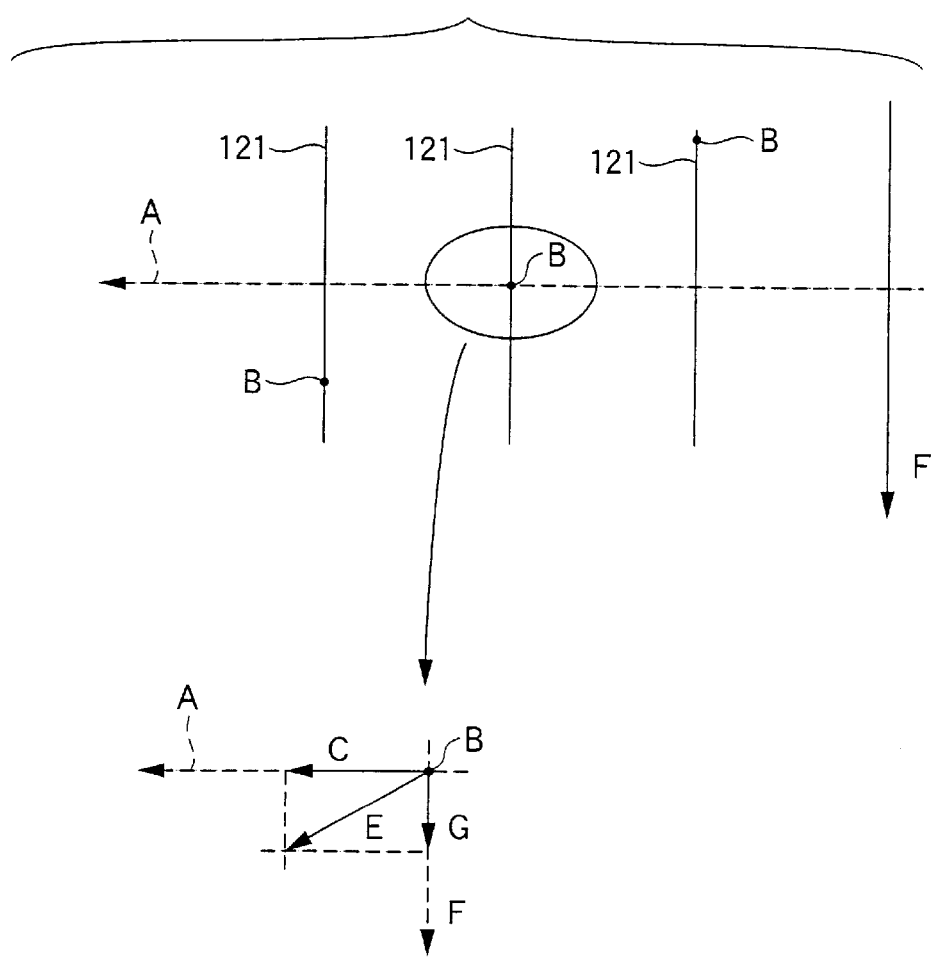
FIG. 30 is a schematic diagram showing a technical concept employed in the fifth embodiment.

This effect is schematically illustrated in FIG. 30. In FIG. 30, character A denotes the direction in which the outer sheath 120 is pushed, i.e. the longitudinal axis direction of the outer sheath 120, character F denotes the direction in which the outer sheath rotates in conjunction with the pushing of the outer sheath 120, i.e. the circumferential direction of the outer sheath 120, and character B denotes the same part of the blade 121 moving in the direction A while rotating in the direction F. By pushing the outer sheath 120, the blade 121 moves in the direction A while rotating in the direction F, and consequently the point B of the blade 21 causes a vector component C along the direction A and a vector component G along the direction F, which are combined together as a cutting force E for positively cutting the tissue 100.

Figure 28:
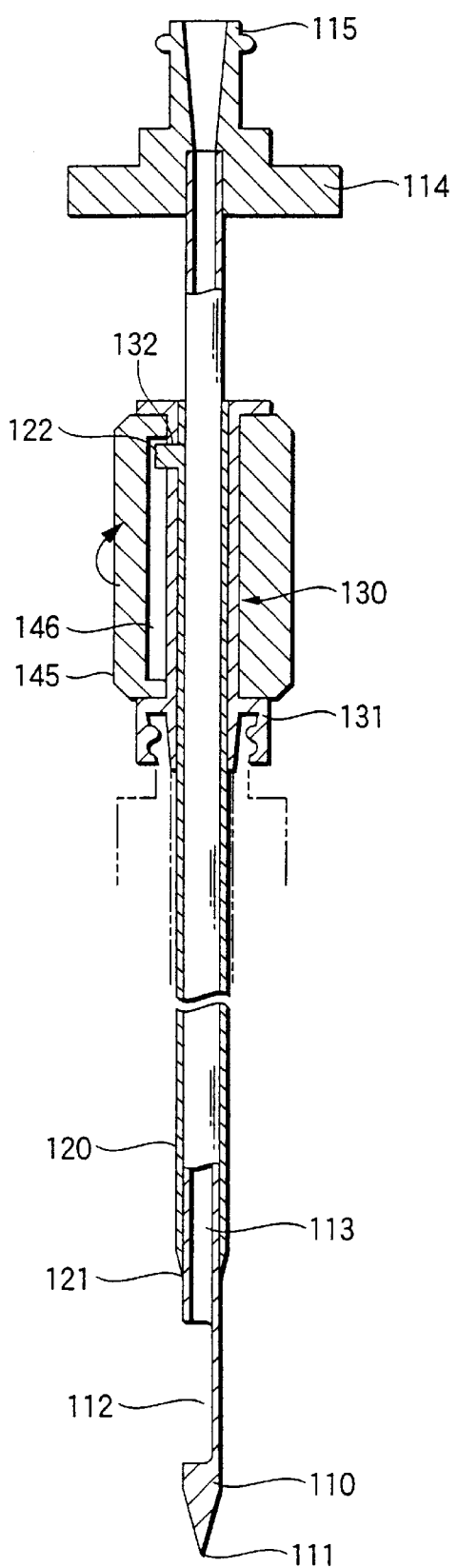
FIG. 28 is a longitudinal section showing an endoscopic tissue collecting instrument according to a sixth embodiment of the invention.

FIG. 28 shows an endoscopic tissue collecting instrument according to a sixth embodiment of the invention, in which the slider knob 140 is replaced by a rotating knob 145.

The rotating knob 145 is mounted on the support tube 130 in such a way that it is unable to move along the longitudinal axis but is capable of rotating about it. The rotating knob 145 has a straight groove 146 (parallel to the longitudinal axis) formed in the inner surface such that it engages the head of the tab 122.

If the operator rotates the knob 145, the outer sheath 120 moves along the longitudinal axis while rotating about it as in the fifth embodiment. Structurally, the sixth embodiment is identical to the fifth embodiment in all other aspects.

In addition, any two or more of the first to fifth embodiments may be combined together as desired. For example, the fifth embodiment may have the saw-toothed blade 21 used in the first embodiment.

What is claimed is:

1. An endoscopic tissue collecting instrument, comprising:
   a needle shaft having a needle tip and a tissue retaining recess behind the needle tip; and
   an outer sheath slidably fitted over the needle shaft, said outer sheath having an outer circumferential portion and having a distal end defining a blade, a diameter of said outer circumferential portion being tapered at said distal end, said outer sheath configured to move relative to said needle shaft to cut off, with said blade, tissue retained in said retaining recess,
   at least a portion of said blade configured to generate a cutting force relative to both a longitudinal axis direction of the outer sheath and a circumferential direction thereof when said outer sheath is moved relative to said needle shaft to cut off, with said blade, tissue retained in said retaining recess.

2. The instrument according to claim 1, wherein the part of the blade is non-perpendicular to the longitudinal axis direction of the outer sheath.

3. The instrument according to claim 1, further comprising:
   a cam system which rotates the blade in the circumferential direction while moving the blade in the longitudinal axis direction.

4. The instrument according to claim 1, wherein said blade is serrated.

5. An endoscopic tissue collecting instrument comprising:
   a needle shaft having a needle tip pointed forward, and a tissue retaining recess recessed laterally in an area close to the needle tip; and
   an outer sheath fitted over the needle shaft so as to be movable back and forth in a longitudinal axis direction relative to the needle shaft, the outer sheath having a blade at its distal end for cutting off a tissue retained in the tissue retaining recess, the outer sheath further having a tapered outer circumferential portion at its distal end,
   wherein the blade formed at the distal end of the outer sheath is oriented obliquely relative to a circumferential direction of the outer sheath.

6. The instrument according to claim 5, wherein a radially inner edge of the distal end of the outer sheath is saw-toothed to define the blade.

7. The instrument according to claim 5, wherein the distal end of the outer sheath is obliquely cut to define the blade.

8. The instrument according to claim 5, wherein said blade is serrated.

9. An endoscopic tissue collecting instrument comprising:
   a needle shaft having a needle tip pointed forward, and a tissue retaining recess recessed laterally in an area close to the needle tip; and
   an outer sheath fitted over the needle shaft so as to be movable back and forth in a longitudinal axis direction relative to the needle shaft, the outer sheath having a blade at its distal end for cutting off a tissue retained in the tissue retaining recess, wherein when the blade is moved across the tissue retaining recess, the outer sheath is rotated about the longitudinal axis direction while being moved in the longitudinal axis direction.

10. The instrument according to claim 9, further comprising:

an aspiration channel extending through said needle shaft, and communicating with a rear of the tissue retaining recess.

11. An endoscopic tissue collecting instrument comprising:

a needle shaft having a needle tip pointed forward, and a tissue retaining recess recessed laterally in an area close to the needle tip; and an outer sheath fitted over the needle shaft so as to be movable back and forth in a longitudinal axis direction relative to the needle shaft, the outer sheath having a blade at its distal end for cutting off a tissue retained in the tissue retaining recess, wherein when the blade is moved across the tissue retaining recess, the outer sheath is rotated about the longitudinal axis direction while being moved in the longitudinal axis direction; and wherein the outer sheath is movably passed through a support tube to be fixed to an entrance of a treatment instrument insertion channel of an endoscope, and a tab projecting from a basal end portion of the outer sheath is in engagement with a spiral groove formed in the support tube.

12. The instrument according to claim 11, further comprising:

a slider knob for manipulation to move the tab in the longitudinal axis direction.

13. The instrument according to claim 11, further comprising:

a rotating knob for manipulation to rotate the tab about the longitudinal axis direction.

14. The instrument according to claim 11, further comprising:

an aspiration channel extending through the needle shaft, and communicating with a rear of the tissue retaining recess.

* * * * *